United States Patent [19]

Cai et al.

[11] Patent Number: 4,877,803
[45] Date of Patent: Oct. 31, 1989

[54] BIS-DIOXOPIPERAZINE DERIVATIVES AND PHARMACEUTICAL COMPOSITIONS CONTAINING THE SAME

[75] Inventors: Jun-Chao Cai; Muneaki Takase, both of Tokyo, Japan

[73] Assignee: Zenyaku Kogyo Kabushiki Kaisha, Tokyo, Japan

[21] Appl. No.: 31,011

[22] PCT Filed: Jun. 25, 1986

[86] PCT No.: PCT/JP86/00324

§ 371 Date: Feb. 24, 1987

§ 102(e) Date: Feb. 24, 1987

[87] PCT Pub. No.: WO87/00170

PCT Pub. Date: Jan. 15, 1987

[30] Foreign Application Priority Data

Jun. 26, 1985 [JP] Japan .............................. 60-139731

[51] Int. Cl.⁴ .................. A61K 31/435; C07D 413/14
[52] U.S. Cl. .............................. 514/227.8; 514/232.2; 514/255; 544/60; 544/121; 544/359; 544/360; 544/364
[58] Field of Search ................. 544/60, 121, 106, 114, 544/119, 359, 360, 364, 385; 514/232.2, 227.8, 255

[56] References Cited

U.S. PATENT DOCUMENTS

4,737,497 4/1988 Ren ..................................... 544/121

OTHER PUBLICATIONS

*Chemical Abstract*, vol. 103, #31960n, Herman, 1985, "Comparison of the Protective Effect of ICRF-187 and Structurally Related Analogs . . . ".

*Primary Examiner*—Richard L. Raymond
*Assistant Examiner*—Raymond Covington
*Attorney, Agent, or Firm*—Scrivener and Clarke

[57] ABSTRACT

Novel bis-dioxopiperazine derivatives represented by the following formula (I) and having a broader antitumor spectrum as well as pharmaceutical compositions containing the compounds as antitumor active components:

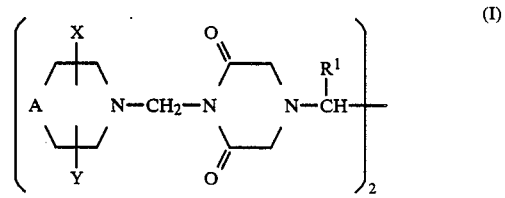

wherein $R^1$ represents a lower alkyl group; A represents an oxygen atom, a sulfur atom or a group of

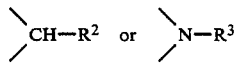

wherein $R^2$ represents a hydrogen atom, a lower alkyl group or phenyl; $R^3$ represents a lower alkyl group, phenyl or benzyl; and X and Y, which are respectively independent and are the same or different, represent a hydrogen atom or a lower alkyl group.

10 Claims, No Drawings

BIS-DIOXOPIPERAZINE DERIVATIVES AND PHARMACEUTICAL COMPOSITIONS CONTAINING THE SAME

TECHNICAL FIELD

The present invention relates to novel bis-dioxopiperazine derivatives having an antitumor activity and pharmaceutical compositions containing the same.

BACKGROUND ART

Several kinds of bis-dioxopiperazine derivatives have been already reported. Among them, especially known as compounds having antitumor activity are 1,2-bis(4-morpholinomethyl-3,5-dioxopiperazin-1-yl)ethane (see Abstract, 8th International Congress of Pharmacology p 441, 1981), dl-1,2-bis(4-morpholinomethyl-3,5-dioxopiperazin-1-yl)propane (see (European Patent Publication No. 0125475A1) and 1,2-bis(4-isobutoxycarbonyloxymethyl-3,5-dioxopiperazin-1-yl)ethane (see Abstract, 14th International Congress of Chemotherapy p 324, 1985 and European Patent Publication No. 0140327A2).

Still, there has been a demand for a bis-dioxopiperazine derivative having more excellent antitumor activity than those known compounds.

DISCLOSURE OF THE INVENTION

Under these circumstances, we, the inventors carried out studies for new bis-dioxopiperazines derivatives and found that the below-mentioned bis-dioxopiperazine derivatives of formula (I) exhibit remarkably excellent antitumor activity, thus completing the present invention.

A compound according to the present invention is represented bythe formula (I):

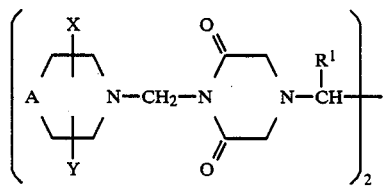
(I)

wherein $R^1$ represents a lower alkyl group; A represents an oxygen atom, a sulfur atom or a group of

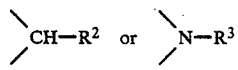

wherein $R^2$ represents a hydrogen atom, a lower alkyl group or phenyl; $R^3$ represents a lower alkyl group, phenyl or benzyl; and X and Y, which are respectively independent and are the same or different, represent a hydrogen atom or a lower alkyl group. The meaning and examples of terms used in this formula will be described.

The wording "lower" refers to a group having 1 to 6 carbon atoms unless otherwise indicated.

The "lower alkyl group" may be selected from the group having a normal or branched carbon chain such as methyl, ethyl, n-prrophyl, isopropyl, n-butyl, isobutyl, tert-butyl, n-pentyl and n-hexyl. Preferably, methyl is used as the lower alkyl group for $R^1$.

The compound according to the present invention is for example as follows:

2,3-bis(4-morpholinomethyl-3,5-dioxopiperazin-1-yl)butane 2,3-bis(4-piperidinomethyl-3,5-dioxopiperazin-1-yl)butane 2,3-bis[4-(4-isopropylpiperidinomethyl)-3,5-dioxopiperazin-1-yl]butane 2,3-bis[4-(3,5-dimethylpiperidinomethyl)-3,5-diosopiperazin-1-yl]butane 2,3-bis[4-(2,4-dimethylpiperidinomethyl)-3,5-dioxopiperazin-1-yl]butane 2,3-bis[4-(4-phenylpiperidinomethyl)-3,5-dioxopiperazin-1-yl]butane 2,3-bis[4-(N-methylpiperazinomethyl)-3,5-dioxopiperazin-1-yl]butane 2,3-bis[4-(N-n-hexylpiperazinomethyl)-3,5-dioxopiperazin-1-yl]butane 2,3-bis[4-(N-phenylpiperazinomethyl)-3,5-dioxopiperazin-1-yl]butane 2,3-bis[4-(N-benzylpiperazinomethyl)-3,5-dioxopiperazin-1-yl]butane 2,3-bis(4-thiomorpholinomthyl-3,5-dioxo-piperazin-1-yl)butane The compound (I) of the present invention has asymmetric carbon atoms in its molecules. It is to be understood that isomers due to such asymmetric carbon atom or combination of any of the isomers are included in the category of the compound (I) of the present invention.

The compound (I) of the present invention may be prepared by reacting a compound represented by the formula (II):

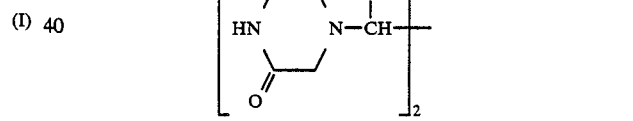

wherein $R^1$ is as defined above, with formaldehyde and a compound represented by the formula (III):

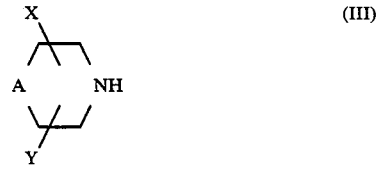

wherein A, X and Y are as defined above.

In this reaction, at least two equivalent molar amounts of the compound of the formula (III) and formaldehyde, respectively, should be used to one molar amount of the compound of the formula (II).

The reaction temperature may range from 25° to 200° C., preferably from 75° to 160° C. and the reaction time may range from 0.5 to 12 hours which depends on reaction temperature.

As for the reaction solvent, polar solvent such as N,N-dimethylformamide (DMF), dimethylsulfoxide (DMSO), acetonitrile, ethyl acetate, methanol, ethanol, butanol or their mixture may be used.

The compound of the formula (II) which is the starting material in the above-mentioned process is a known compound and can be prepared according to a process described in British Patent Specification No. 1234935.

The antitumor activity of the compound of the formula (I) according to the present invention, which is prepared by the above-mentioned process, was verified by the below-mentioned tests. The test compounds in these tests were as follows:

(1) meso-2,3-bis(4-morpholinomethyl-3,5-dioxopiperazin-1-yl)butane
(2) meso-2,3-bis(4-thiomorpholinomethyl-3,5-dioxopiperazin-1-yl)butane
(3) meso-2,3-bis[4-(N-phenylpiperazinomethyl)-3,5-dioxopiperazin-1-yl]butane
(4) meso-2,3-bis(4-piperoidinomethyl-3,5-dioxopiperazin-1-yl)butane
(5) meso-2,3-bis[4-(3,5-dimethylpiperidinomethyl)-3,5-dioxopiperazin-1-yl]butane Comparative Compounds
(A) 1,2-bis(4-morpholinomethyl-3,5-dioxopiperazin-1-yl)ethane
(B) dl-1,2-bis(4-morpholinomethyl-3,5-dioxopiperazin-1-yl)propane (I) Growth Inhibition of Tumor Cells in Vitro:

Tumor cells were collected aseptically with capillary tube from ascites in $CDF_1$ male mice transplanted intraperitoneally with $1 \times 10^6$ cells of P388 lymphocytic leukemia 5 days Before. Cell suspension was prepared at $5 \times 10^4$ cells/0.5 ml in a RPMI1640 medium supplemented with 10% fetal calf serum, Kanamycin (0.1 mg/ml) and 2-hydroxyethyldisulfide (0.01 mm). Each sample was dissolved or suspended in the medium at a concentration of $1 \times 10^{-1} - 1 \times 10^{-5}$ mM/ml.

A test tube with Molton stopper loosely involving 0.5 ml each of the cell suspension and the sample suspension was kept for 48 hours at 37° C. in an incubator supplied with air containing 5% carbon dioxide. Then, after addition of 4 ml of 0.25% trypsin solution, the tube was shaken for 5 minutes at 37° C. The cells harvested therefrom was counted by using of a Coulter Counter and the inhibition of cell growth was calculated by the following formula:

$$\text{Growth Inhibition (\%)} = \left(1 - \frac{T}{C}\right) \times 100$$

T: number of cells in the culture containing test compound.
C: number of cells in the culture of control 50% Inhibitory concentration of cell growth ($IC_{50}$) was calculated based on the inhibition in various concentrations of test compound and is shown in Table I.

TABLE 1

| Test Compound | $IC_{50}$ (mM) |
|---|---|
| (1) | $6.1 \times 10^{-5}$ |
| (2) | $2.3 \times 10^{-4}$ |
| (3) | $2.2 \times 10^{-5}$ |
| (4) | $4.7 \times 10^{-5}$ |
| (5) | $1.2 \times 10^{-5}$ |
| (A) | $2.4 \times 10^{-3}$ |
| (B) | $1.6 \times 10^{-3}$ |

It was found that the compounds of the present invention exhibit remarkably strong growth inhibition activity against P388 lymphocytic leukemia cells and are effective in concentration about one-tenth to about one-hundredth as little as that of the structurally analogous comparative compound A or B.

(II) Increase in Life Span on Tumor-transplanted Mouse: The treated group to which the compound of the present invention was administered consisted of seven mice, while the control group consisted of ten mice. Six weeks old male mice ($CDF_1$, $25\pm2$ g of body weight) were employed as host animals.

Tumor cells ($1.0 \times 10^6$) of P388 lymphocytic leukemia were transplanted intraperitoneally into each mouse. The treatment was effected one day after the transplantation and on 5th day by administering prescribed dose of each test compound intraperitoneally to the mice.

Antitumor activity of the test compound was evaluated by the rate of increase in life span (ILS) which was calculated with the following formula.

$$ILS\,(\%) = \left(\frac{T'}{C'} - 1\right) \times 100$$

T': median survival time of treated mice
C': median survival time of control mice The results obtained from the above-mentioned test are shown in Table 2.

TABLE 2

| Test Compound | Daily Dose (mg/kg) | ILS (%) |
|---|---|---|
| (1) | 3.0 | 165 |
| (2) | 1.8 | >194 |
| (3) | 3.4 | 78 |
| (A) | 100* | 60 |
|  | 3.0 | 2 |
| (B) | 200* | 47 |
|  | 3.0 | 1 |

*Adequate dose

Against P388 lymphocytic leukemia, the compounds of the present invention exhibit remarkably strong antitumor activity in comparison with the Comparative Compounds A and B. More specifically, the compound of the present invention exhibits remarkably excellent ILS (%) by dose about one-thirtieth to about one-hundred and tenth as little as the adequate dose of the Comparative Compound A or B.

It was found that the compounds of the present invention are effective by daily dose of 0.5 or 1 mg/kg in antitumor activity tests using L1210 lymphoid leukemia, B-16 melanoma, Lewis lung carcinoma, MM-46 mammary carcinoma, MH-134 hepatoma and Ehrlich carcinoma and have a broader antitumor spectrum.

The acute toxicity of the compounds of the present invention was examined by the following test.

The test group to which the compound of the present invention was administered consisted of ten mice. Five weeks old male mice (ICR, $25\pm2$ g of body weight) were employed as test animals.

These animals were intraperitoneally given the test compound which was suspended in the saline solution containing carboxymethyl cellulose (CMC) by 0.5% and were observed for 14 days successively, and $LD_{50}$ value of acute toxicity was determined by Litchfield-Wilcoxon method. As a result, $LD_{50}$ for meso-2,3-bis(4-morpholinomethyl-3,5-dioxopiperazin-1-yl)butane was 10.7 mg/kg.

The following descriptions are given for the administration routes, pharmaceutical forms and doses when bis-dioxopiperazine derivatives of the present invention are applied to human.

The compounds of the present invention may be administered orally in forms such as tablets, coated tablets, powders, granules, capsules, microcapsules, syrups and so on. They may be also administered parenterally in forms such as injections which may include dissolvable freeze-drying form, suppositories and so on.

In the preparation of these forms, pharmaceutically acceptable diluent bases, binders, disintegrators, lubricants, suspensions, emulsifiers, antiseptics, stabilizers and dispersing agents, for example lactose, sucrose, starch, dextrin, crystalline cellulose, kaolin, calcium carbonate, talc, magnesium stearate, distilled water and physiological saline solution may be used.

Although the daily doses of these compounds may be varied according to the conditions, ages and weights of the subjects to be treated, the daily doses to adult humans may normally fall within the range of 1 to 600 mg, preferably 5 to 100 mg, and may be divided into two or three portions.

BEST MODE FOR CARRYING OUT THE INVENTION

The invention is illustrated by the following example, but it should be noted that the present invention is not limited to the example.

EXAMPLE 1

Meso-2,3-bis(4-morpholinomethyl-3,5-dioxopiperazin-1-yl)butane

A mixture of meso-2,3-bis(3,5-dioxopiperazin-1-yl)butane (0.50 g, 1.8 mmol), morpholine (3 ml, 34 mmol) and anhydrous ethanol (6 ml) was refluxed. To the mixture, 37% aqueous formaldehyde solution (4 ml) was added gradually, and then the mixture was refluxed for 30 minutes. The reaction mixture was filtered and the filtrate was allowed to stand in a refrigerator overnight. The resulting precipitates were collected by filtration and washed with ethanol to give the titled compound (0.45 g; yield 53%).

Melting Point: 205°–206° C. (recrystallized from ethyl acetate),

Elementary Analysis (%) Calculated for $C_{22}H_{36}O_6N_6$: C 54.98; H 7.55; N 17.49, Found: C 54.80; H 7.51; N 17.52, Nuclear Magnetic Resonance (NMR) Spectrum ($CDCl_3$) δ ppm: 1.05 (6H, d, J=6 Hz), 2.5–2.6 (10H, m), 3.39 (4H, d, J=16 Hz), 3.47 (4H, d, J=16 Hz), 3.6–3.7 (8 H, m), 4.74 (4H, s).

In accordance with the procedure of the Example 1, the following compounds were obtained from the corresponding starting materials.

Meso-2,3-bis(4-piperidinomethyl)-3,5-dioxopiperazin-1-yl)butane (yield 52)

Melting Point: 156°–160° C.

Infrared Absorption (IR) Spectrum (KBr) cm$^{-1}$: 1680, 1725 (C=O).

NMR Spectrum ($CDCl_3$) δ ppm: 1.06 (6H, d, J=5 Hz), 1.35 (4H, m), 1.53 (8 H, m), 2.53 (8H, m), 2.62 (2H, m), 3.38 (4H, d, J=16 Hz), 3.50 (4H, d, J=16 Hz), 4.76 (4H, s).

Meso-2,3-bis[4-(3,5-dimethylpiperidinomethyl)-3,5-dioxopiperazin-1-yl]butane (yield 43%)

Melting Point: 182°–184° C.

IR Spectrum (KBr) cm$^{-1}$: 1680, 1730 (C=O),

NMR Spectrum ($CDCl_3$) δ ppm: 0.8–1.0 (12H, m), 1.05 (6H, d, J=6 Hz), 1.5–1.7 (8H, m), 1.8–3.0 (10H, m), 3.37 (4H, d, J=16 Hz), 3.47 (4H, d, J=16 Hz), 4.77 (4H, s).

Meso-2,3-bis[4-(N-phenylpiperazinomethyl)-3,5-dioxopiperazin-1-yl]butane (yield 28%)

Melting Point: 167°–172° C.

IR Spectrum (KBr) cm$^{-1}$: 1680, 1730 (C=O),

NMR Spectrum (DMSO-$d_6$) δ ppm: 0.91 (6H, d, J=5 Hz), 2.60 (8H, m), 2.79 (2H, m), 3.07 (8H, m), 3.41 (4H, d, J=16 Hz), 3.52 (4H, d, J=16 Hz), 4.65 (4H, s), 6.7–7.2 (10H, m).

Meso-2,3-bis(4-thiomorpholinomethyl-3,5-dioxopiperazin-1-yl)butane (yield 76%)

Melting Point: 218°–220° C.

IR Spectrum (KBr) cm$^{-1}$: 1680, 1730 (C=O).

NMR Spectrum ($CDCl_3$) δ ppm: 1.06 (6H, d, J=5 Hz), 2.5–2.7 (10H, m), 2.8–3.0 (8H, m), 3.37 (4H, d, J=16 Hz), 3.48 (4H, d, J=16 Hz), 4.75 (4H, s).

CAPABILITY OF EXPLOITATION IN INDUSTRY

As is clear from the foregoing, the compounds (I) of the present invention are novel compounds different in structure from the known bis-dioxopiperazine derivatives, have a broader antitumor spectrum and exhibit by far excellent antitumor activity in comparison with the known antitumor bis-dioxopiperazine (Comparative Compound A or B). Thus, the compounds of the present invention have wider pharmaceutical usages an antitumor agents.

We claim:

1. A compound represented by the formula (I):

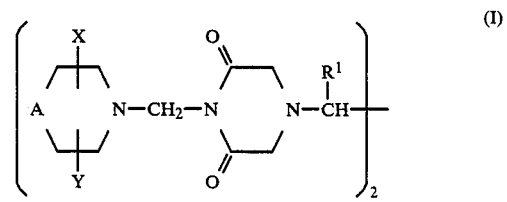

wherein $R^1$ represents a lower alkyl group; A represents an oxygen atom, a sulfur atom or a group of

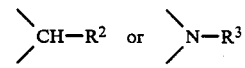

wherein $R^2$ represents a hydrogen atom, a lower alkyl group or phenyl; $R^3$ represents a lower alkyl group, phenyl or benzyl; and X and Y, which are respectively independent and are the same or different, represent a hydrogen atom or a lower alkyl group.

2. The compound according to claim 1, wherein $R^1$ is methyl.

3. The compound according to claim 1, wherein A is an oxygen atom, a sulfur atom or a group of —$CH_2$— or

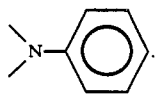

4. The compound according to claim 1, wherein R¹ is methyl; and A is an oxygen atom, a sulfur atom or a group of —CH₂— or

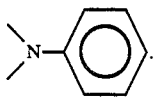

5. The compound according to claim 1, wherein R¹ is methyl; A is an oxygen atom; and X and Y are both a hydrogen atom.

6. The compound according to claim 1, wherein R¹ is methyl; A is a sulfur atom; and X and Y are both a hydrogen atom.

7. The compound according to claim 1, wherein R¹ is methyl; A is a group of —CH₂—; and X and Y are both a hydrogen atom.

8. The compound according to claim 1, wherein R¹ is methyl; A is a group of —CH₂—; and X and Y are both methyl.

9. The compound according to claim 1, wherein R¹ is methyl; A is a group of

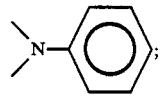

amd X amd Y are both a hydrogen atom.

10. A pharmaceutical composition containing a compound as described in claim 1 as an antitumor active component and a pharmaceutically acceptable diluent or carrier.

* * * * *